United States Patent
Karnieli

(10) Patent No.: US 6,508,762 B2
(45) Date of Patent: Jan. 21, 2003

(54) METHOD FOR MONITORING FOOD INTAKE

(76) Inventor: Eddy Karnieli, 59A KKL Street, Kiryat Tivon 36082 (IL)

( * ) Notice: Subject to any disclaimer, the term of this patent is extended or adjusted under 35 U.S.C. 154(b) by 0 days.

(21) Appl. No.: 09/922,787

(22) Filed: Aug. 7, 2001

(65) Prior Publication Data

US 2002/0022774 A1 Feb. 21, 2002

(30) Foreign Application Priority Data

Aug. 8, 2000 (IL) .................................................. 137759

(51) Int. Cl.[7] .................................................. A61B 5/00
(52) U.S. Cl. ........................ 600/300; 434/127; 128/921
(58) Field of Search ................................ 600/300, 301; 128/897, 898, 921, 922, 923; 426/2; 434/127; 382/110; 705/15, 27

(56) References Cited

U.S. PATENT DOCUMENTS

| | | | |
|---|---|---|---|
| 4,686,624 A | | 8/1987 | Blum et al. |
| 4,796,182 A | | 1/1989 | Duboff |
| 4,951,197 A | | 8/1990 | Mellinger |
| 5,173,588 A | | 12/1992 | Harrah |
| 5,233,520 A | | 8/1993 | Kretsch et al. |
| 5,398,688 A | | 3/1995 | Laniado |
| 5,412,564 A | | 5/1995 | Ecer |
| 5,478,989 A | * | 12/1995 | Shepley ................. 235/375 |
| 5,542,420 A | * | 8/1996 | Goldman et al. ........... 600/301 |
| 5,819,735 A | | 10/1998 | Mansfield et al. |
| 5,836,312 A | * | 11/1998 | Moore ................. 128/897 |
| 5,839,901 A | | 11/1998 | Karkanen |
| 5,845,263 A | * | 12/1998 | Camaisa et al. ........... 705/15 |
| 6,336,136 B1 | * | 1/2002 | Harris ................. 128/921 |
| 6,349,526 B1 | * | 2/2002 | Newman ................. 53/504 |

* cited by examiner

Primary Examiner—Eric F. Winakur
Assistant Examiner—David J. McCrosky
(74) Attorney, Agent, or Firm—Eitan, Pearl, Latzer & Cohen-Zedek

(57) ABSTRACT

The invention provides a method and a system for dietary control. The method provides information to a person under dietary limitations prior to and during a meal regarding an item positioned before the person in real time. The system includes, in combination, a video photographic means connected to a computer provided with a suitable database and further provided with a display unit connected to the computer.

12 Claims, 3 Drawing Sheets

METHOD FOR MONITORING FOOD INTAKE

RELATED APPLICATIONS

This application claims priority of Israeli application number 137759, filed on Aug. 8, 2000, which is incorporated in its entirety by reference herein.

BACKGROUND OF INVENTION

The present invention relates to dietary control.

More particularly, the invention provides a computerized method for identifying foods about to be eaten and providing information and warnings if eating such food would violate the specific dietary restrictions applicable to the person using the method. Dietary restrictions are usually applicable to persons who need to or want to lose weight aid to patients suffering from certain illnesses. For example, obese people are limited in calorie intake, while diabetic patients need to control free sugar consumption.

Recommended calorie intake is about 70% of the basal metabolic rate, or it can be set at 25 kcal/kg of ideal boded weight, i.e. 1200–1500 calories per day. Such calorie intake is difficult to monitor, follow and maintain. Further examples of necessary dietary restraints relate to high fats for hyperlipidemic patients and to sodium for patients with hypertension.

Much effort has already been expended in developing solutions for maintaining eating restrictions as well as devices assisting shoppers to chose suitable food items regarding the food item constituents.

In U.S. Pat. No. 4,686,624 Blum et al. disclose a portable apparatus for acquiring and processing dietary information. The apparatus includes a keyboard, software, ROM and RAM memories, a clock, and a communication device, and provides instructions to the user. There is however no means of automatic food identification; the user must classify and type in this data.

The electronic calculator proposed by Duboff in U.S. Pat. No. 4,796,182 requires the user to enter a figure representing food consumed. The calculator then subtracts the entry from the daily allowance and displays the result. The obvious problem is that users need to estimate the calorie content of consumed food.

The weight loss management system disclosed by Mellinger in U.S. Pat. No. 4,951,197 generates a menu tailored to a specific user. The system is in effect a software program.

Harrah proposes a combination of a guide book and a mechanical calculator in U.S. Pat. No. 5,173,588. The user registers his consumption of a food item by rotating a dial by an amount specified in the guidebook.

A more ambitious system is proposed by Kretch et al. in U.S. Pat. No. 5,233,520. A computer is coupled to an electronic scale, and input elements inform the computer what is being weighed. Software converts this information into instructions relevant to the needs of the user.

In U.S. Pat. No. 5,398,688 Laniado proposes a system which indicates allowed time for eating. Normal eating rates are calculated from an empirical relationship for a particular individual between a change in a physiological variable and a rate and/or amount of food intake. It Is not clear how different foods aid eating interruptions are to be handled.

Ecer in U.S. Pat. No. 5,412,564 discloses a system intended to assist in diet control at the rime food items are purchased. The system uses a portable computer, a smart card and a bar code reader, and prints out a report at the conclusion of purchase. As consumers usually shop for more than one person, such system appears to be of limited application.

A cumulative total of consumed calories and other nutrients is claimed to be provided by an electronic device disclosed by Mansfield et al. in U.S. Pat. No. 5,819,735. The device includes a barcode reader for prepared packaged foods and a printed generic food barcode list provided with the device. The entered information is processed and various results displayed. Most foods being served do not have a barcode, and the continuous search through the provided list for the relevant barcode will become tiresome.

In U.S. Pat. No. 5,839,901 Karkanen discloses several embodiments of an integrated weight loss control method. The method requires the individual to input much data, which is likely to become so tiresome that the weight-loss plan is likely to be abandoned.

OBJECTS OF THE INVENTION

It is therefore one of the objects of the present invention to obviate the disadvantages of prior art diet information systems and to provide a method and system which uses machine vision to identify foods, to calculate and monitor their caloric value, and to provide tools for adjusting food consumption according to a predetermined regimen while relieving the user of part of the task of data entry.

The present invention achieves the above objects by providing a method for providing information to a person under dietary limitations, prior and during a meal, regarding a food item positioned before said person, and making available in real time guidance messages relating thereto, said method comprising the steps:

a) providing the user with video photographic means and directing same ill the direction of food items;

b) correlating pictures obtained in step a) with electronically-stored pictures of food items for identification thereof, c) correlating said identified food item with information stored in a data base regarding the content of the identified food regarding carbohydrates, protein, fat, amino acids and food constituents whichever is important for the person being monitored;

d) correlating information obtained in step c) with preprogrammed dietary restrictions of the person being monitored; and e) generating a display message for the user including warnings and instructions regarding eating limitations for the photographed food item.

In a preferred embodiment of the present invention there is provided a method wherein at least a part of the required equipment for application of said method, including a video camera, earphones, and computing means is worn on the body of the person being monitored.

In a most preferred embodiment of the present invention there is provided a method wherein step e) is carried out at least in part by means of a two-way communication link with a remote source.

The inventor further provides a system which comprises in combination a video photographic means connected to a computer provided with a database and a display means connected to said computer.

It will thus be realized that the novel method and system of the present invention serves to increase the probability that the patient will persevere in keeping to a prescribed diet because fewer data entry tasks need be performed in the monitoring system of the present invention. The data which does need to be entered into the system program can be inputted by medical personnel before use of the system. Thus the method of the present invention may be used by persons unable to input data or use computer-like devices.

SHORT DESCRIPTION OF DRAWINGS

The invention will now be described further with reference to the accompanying drawings, which represent by example preferred embodiments of the invention. Structural details are shown only as far as necessary for a fundamental understanding thereof. The described examples, together with the drawings, will make apparent to those skilled in the art how further forms of the invention may be realized.

DETAILED DESCRIPTION OF PREFERRED EMBODIMENT

Figure 1:
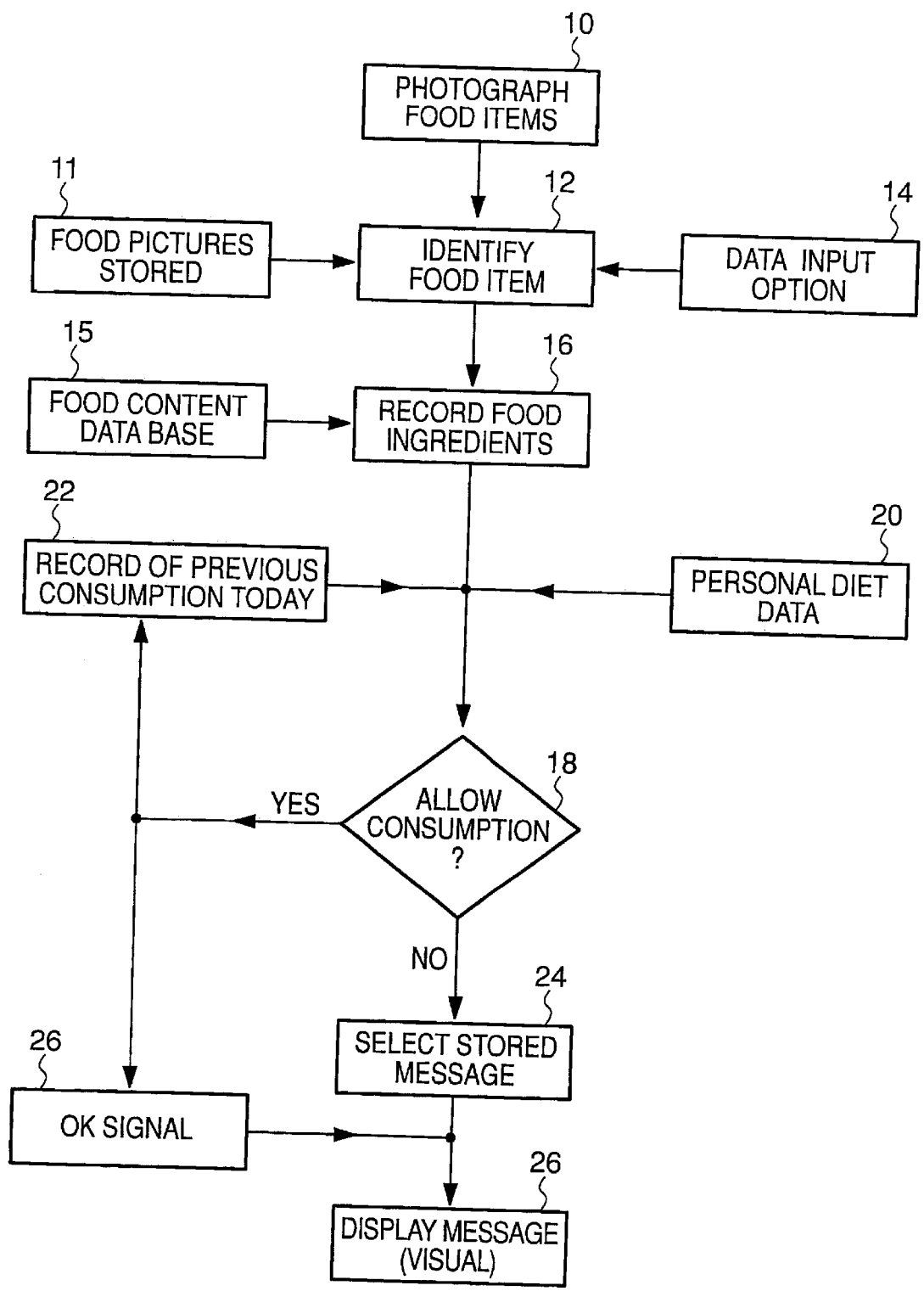
FIG. 1 is a block diagram of a preferred embodiment of the method according to the invention.

There is seen in FIG. 1 a representation of a method for providing information to a person under dietary limitations. Such restrictions may be necessary because the person is obese or diabetic, or for other reasons.

Instructions are provided prior and during a meal, regarding a food item positioned before the person about to eat. The method makes available in real time audible or visual guidance messages relating thereto.

The method represented in FIG. 1 comprises the following steps.

STEP A. Providing the user with video photographic means and directing same in the direction of food items 10.

In the present embodiment of the invention photographic means is a hand-held video camera which the user points at the food intended to be eaten. The camera is part of a machine vision system and is connected to a computer for analysis. Instead of the camera a hand-held scanner may be used.

STEP B. Correlating pictures obtained in STEP A with electronically-stored pictures of food items 11 for identification thereof 12.

Data input means 14, such as a keyboard, provided to the user is generally idle. However should the software fail to identify a particular food item, the user has the option of inputting this information manually.

STEP C. Correlating and recording the identified food item with information stored in a data base 15 regarding the content of the identified food 16 regarding carbohydrates, protein, fat, amino acids and food constituents whichever is important for the person being monitored.

STEP D. Correlating information 16 obtained in STEP C with preprogrammed dietary restrictions 20 of the person being monitored. The information 20 may be stored in the database of a website, and is available to the patient and his/her doctors. Account is taken of previous food consumption 22 during the day to allow or forbid consumption.

STEP E. Generating a display message 24 for the user including warnings and instructions regarding eating limitations for the photographed food item.

A typical message might be "Identified coffee or tea with mill. The OK signal given is conditional on no sugar added. For sweetener use saccharine."

If an OK signal 26 is issued for consumption of a food item, the food item is registered as consumed in the data base of previous food consumption 22 and its constituents will be added and recorded in the database relating to the user and the current date. In the present embodiment the message display 24 is visual.

With reference to the rest of the figures, similar reference numerals have been used to identify similar parts.

In a second embodiment of the method, part of the required equipment, including a small wearable and portable computer unit, for its application is worn on the body of the person 28 being monitored, and messages in audible form are received by the user through earphones 30.

Figure 2:
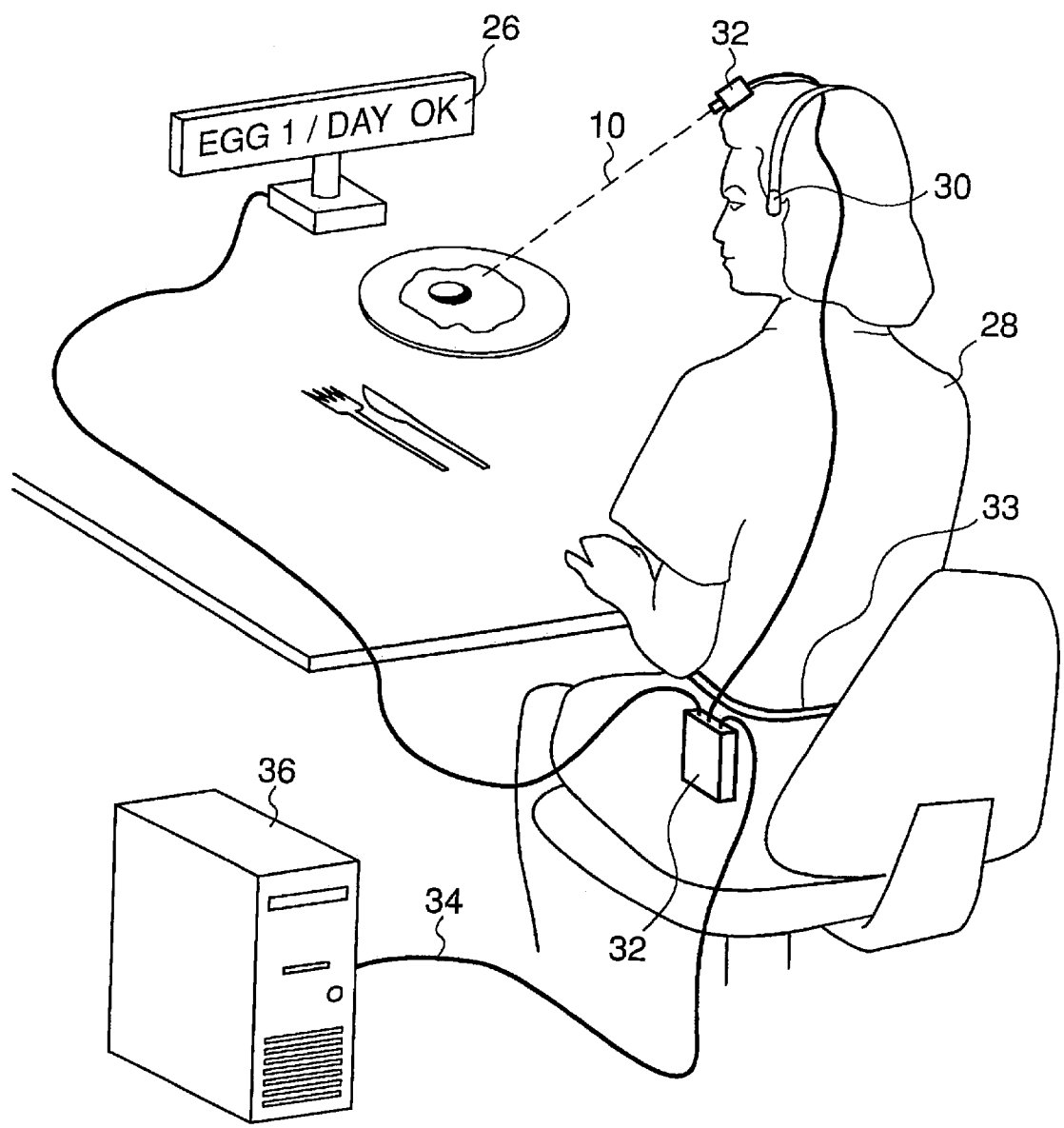
FIG. 2 is a pictorial view showing an application of the method where some equipment items are body worn.

Referring now to FIG. 2, there is seen a person 28 under dietary supervision wearing a small head-mounted video camera 32. Earphones 30 are worn in the usual manner Computing means 32 are attached to the belt 33. A data transfer cord 34 connects computing means to a main computer 36.

Except that in the present embodiment the message display is also auditory, and that some of the equipment is carried by the body of the user, the method remains as described with reference to FIG. 1.

Figure 3:
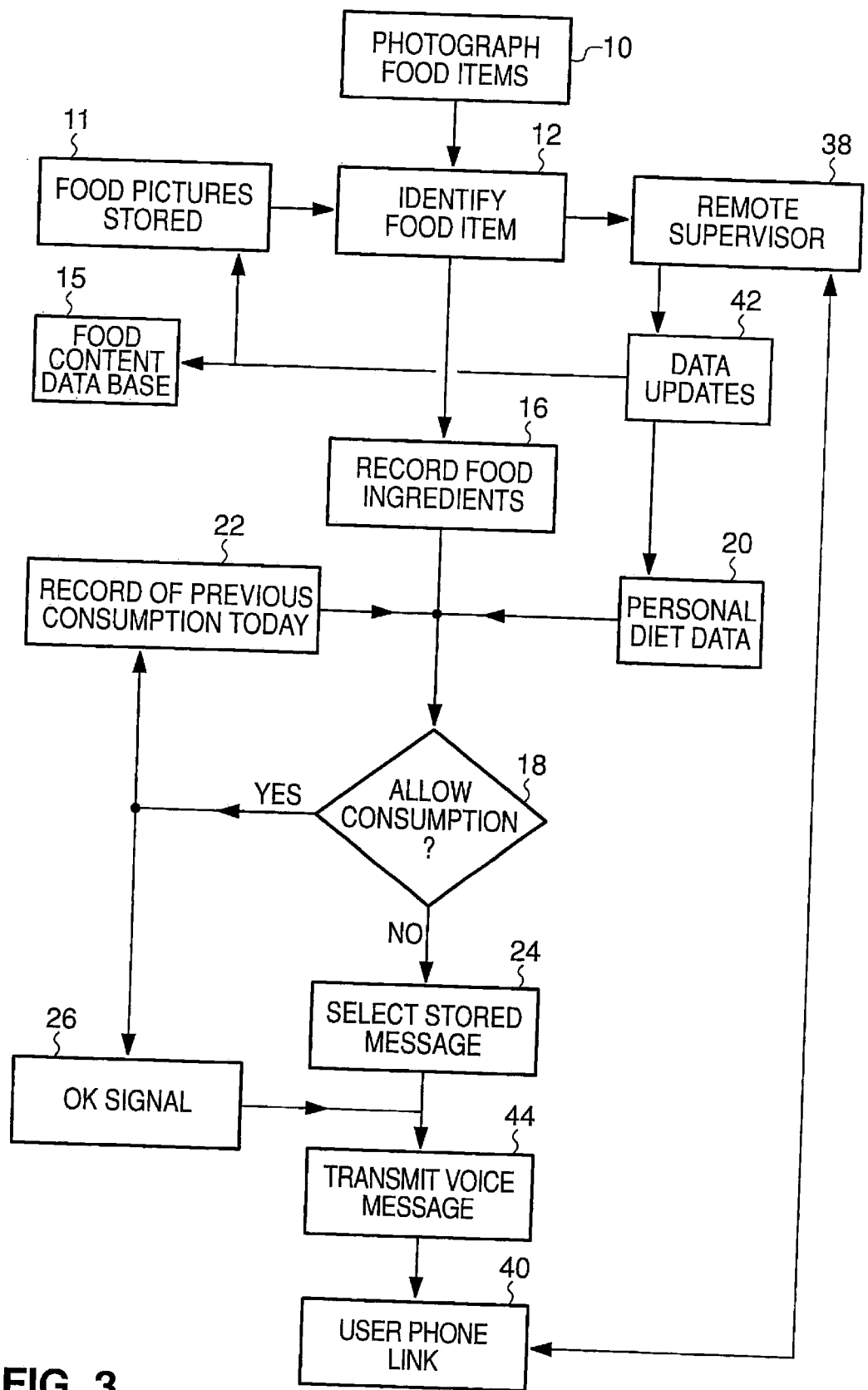
FIG. 3 is a block diagram of a further embodiment of the method including a remote supervisor.

FIG. 3 is a representation of a third embodiment of the method of the invention, wherein provision is made for on-line advice message 24 by a remote supervisor 38 in addition to automated advice generated by the computer program. Such on-line connection is established through a user telephone link 40, either by line telephone or radio telephone, and is of particular value for closer supervision of patients and for giving advice when unexpected problems occur, typically regarding new or unexpected food items not included in the data base or food items which the vision system failed to identify.

The supervisor is furthermore provided with means for issuing data updates 42. In the present embodiment of the method the automatically selected message 24 is transmitted to the user in voice form 44.

The scope of the described invention is intended to include all embodiments coming within the meaning of the following claims. The foregoing examples illustrate useful forms of the invention, but are not to be considered as limiting its scope, as those skilled in the art will readily be aware that additional variants and modifications of the invention can be formulated without departing from the meaning of the following claims.

I claim:

1. A method for providing information to a person under dietary limitations, prior and during a meal, regarding a food item positioned before said person, and making available in real time guidance messages relating thereto, said method comprising the steps:

a) providing the user with video photographic means and directing same in the direction of said food item;

b) correlating pictures obtained in step a) with electronically-stored pictures of reference food items thereby to identify said food item;

c) correlating said identified food item with information stored in a data base regarding the content of the identified food item;

d) correlating information obtained in step c) with preprogrammed dietary restrictions of the person being monitored; and e) generating a display message for the user regarding eating limitations related to the photographed food item.

2. The method as claimed in claim 1, wherein at least a part of the required equipment for application of said method, including a video camera, earphones, and computing means is worn on the body of the person being monitored.

3. The method as claimed in claim 1, wherein step e) is carried out at least in part by means of a two-way communication link with a remote source.

4. The method as claimed in claim 1, wherein said user is obese.

5. The method as claimed in claim 1, wherein said user is diabetic.

6. A method according to claim 1 wherein said information regarding the content of the identified food item comprises information regarding food constituents of the identified food item, said food constituents comprising at least one constituent selected from the group including carbohydrates, protein, fat, and amino acids.

7. A system for dietary control comprising:
   video photographic means to obtain pictures of a food item;
   a computer;
   a data base associated with said computer; and
   a display associated with said computer,
   wherein said computer is adapted to receive the pictures obtained by said video photographic means, to identify said food item by correlating the pictures obtained by said video photographic means with pre-stored pictures of a plurality of reference food items, to correlate said identified food item with information stored in said data base regarding the content of the identified food item, to correlate the information regarding the content of the identified food item with preprogrammed dietary restrictions of the person being monitored, and to generate on said display a message relating to said dietary restrictions.

8. A system as claimed in claim 7 wherein at least part of the system, including said video photographic means and said computer, is worn on the body of the person being monitored.

9. A system as claimed in claim 7, wherein at least part of the system is located at a remote site and wherein said computer communicates with said remote site by means of a two-way communication link.

10. A system as claimed in claim 7, wherein said user is obese.

11. A system as claimed in claim 7, wherein said user is diabetic.

12. A system according to claim 7 wherein said information regarding the content of the identified food item comprises information regarding food constituents of the identified food item, said food constituents comprising at least one constituent selected from the group including carbohydrates, protein, fat, and amino acids.

* * * * *